United States Patent [19]

Bardy et al.

[11] 4,057,615

[45] Nov. 8, 1977

[54] METHOD OF TAGGING EXCIPIENTS WITH $^{99m}$TECHNETIUM

[75] Inventors: André Bardy, Morangis; Jacqueline Beydon; Renée Gobin, both of Paris; Michel Hegesippe, Cernay-la-Ville, all of France

[73] Assignee: Commissariat a l'Energie Atomique, Paris, France

[21] Appl. No.: 599,977

[22] Filed: July 29, 1975

[30] Foreign Application Priority Data

Aug. 6, 1974 France .................................. 74.27249

[51] Int. Cl.$^2$ .................... A61K 29/00; A61K 43/00; G01T 1/161
[52] U.S. Cl. .................. 424/1; 260/429 R; 424/9
[58] Field of Search .................. 424/1, 1.5, 9; 260/429 R, 429 L

[56] References Cited

U.S. PATENT DOCUMENTS

| 3,735,001 | 5/1973 | McRae et al. | 424/1 |
| 3,740,418 | 6/1973 | Rajamani et al. | 424/1 |
| 3,873,680 | 3/1975 | Jackson et al. | 424/1 |

OTHER PUBLICATIONS

Eckelman et al., Journal of Nuclear Medicine, vol. 12, No. 11, 1971, pp. 707–710.
Hegesippe et al., Journal of Nuclear Biology and Medicine, vol. 17, No. 3, 1973, pp. 93–96.
Zolle et al., International Journal of Applied Radiation and Isotopes, vol. 21, 1970, pp. 155–167.
Bardy et al., Journal of Nuclear Medicine, vol. 16, No. 5, 1975, pp. 435–437.
Hosain, Nuclear Science Abstracts, vol. 28, No. 12, Dec. 31, 1973, p. 2908, Abstract No. 30395.
Hegesippe et al., Nuclear Science Abstracts, vol. 29, No. 11, June 15, 1974, p. 2580, Abstract No. 26715.

*Primary Examiner*—Benjamin R. Padgett
*Assistant Examiner*—Christine M. Nucker
*Attorney, Agent, or Firm*—Lane, Aitken, Dunner & Ziems

[57] ABSTRACT

A method of using $^{99m}$ technetium for tagging excipients in medical diagnosis by scintigraphy comprises mixing, in an aqueous solution of alkali-metal pertechnetate, an excipient and a reducing agent in the form of a complex, which complex is such that the association constant of the anion with reduced technetium is less than the association constant of the excipient with reduced technetium, thereby forming a radio-pharmaceutical substance which is a complex between the excipient and $^{99m}$ technetium.

7 Claims, 1 Drawing Figure

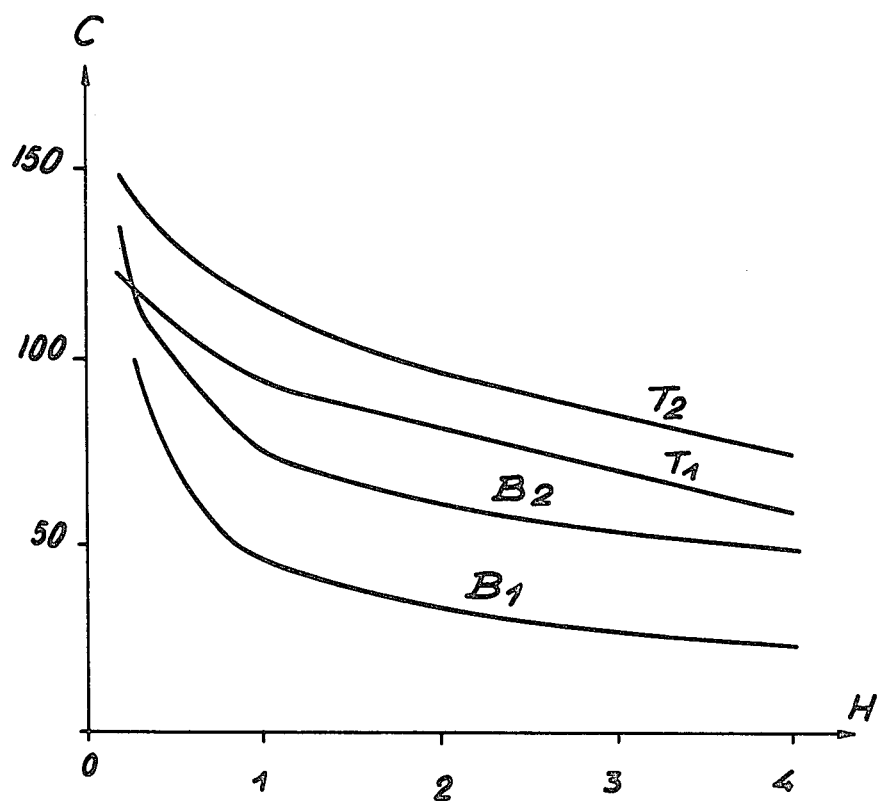

METHOD OF TAGGING EXCIPIENTS WITH 99M TECHNETIUM

This invention relates to a method of using $^{99m}$ technetium for tagging excipients so as to obtain radio-pharmaceutical substances for medical use in diagnosis by scintigraphy.

BRIEF DISCRIPTION OF THE DRAWINGS

The single FIGURE is a graph showing time variations of elimination of pyrotechnetate vs. a tagged Tc-99m bleomycin complex from the blood.

Radio-pharmaceutical substances, after being injected into the blood, tend to accumulate in certain regions of the organism, in accordance with a tropisim which is peculiar to themselves. They can be detected by scintigraphy so as to show up certain organs and locate tumours or other anomalies.

The use of $^{99m}$Tc in nuclear medicine has developed continuously for several years. This development is due to the fact that the nuclear and chemical properties of $^{99m}$Tc are particularly suited to radiodiagnostic requirements.

Its gamma radiation (140 Kev) is suitable for the detectors used and its period (6 hours) is sufficient for conveniently carrying out medical examinations while avoiding any residual activity in vivo and avoiding any risk of contamination. The absence of any high-energy gamma component is also advantageous, both for the patient and for the manipulator.

The preparation of $^{99m}$Tc is particularly easy, since it can be extracted from $^{99}$Mo, using generators currently sold on the international market by a number of manufacturers, and can be obtained by simple elution in the form of pertechnetate in sterile, neutral, isotonic solution.

Chemically, technetium is a transition metal, a homologue of manganese and rhenium, which it resembles in the number of its valencies.

At valency VII, the most stable one, it occurs in the form of a pertechnetate and its biochemical properties in this state are suitable for use in certain research on thyroid and cerebral function.

At lower valencies, it can form relatively stable complexes with a number of mineral, organic or biochemical compounds. In the latter case its chemical state is often very uncertain; it is probably in the form of a cationic species, the Tc being combined with the compound via electron-donor groups of chelating molecules.

Methods of tagging with $^{99m}$ technetium, wherein stannous chloride is used as the reducing agent, are described e.g. in U.S. Pat. No. 3,725,295 and Continuation in part Ser. No. 455.005 filed Mar. 26, 1974, now U.S. Pat. No. 3,931,396.

The most common method of tagging consists in adding the excipient and a solution of SnCl$_2$ in an acid medium to an alkali-metal pertechnetate solution, followed by neutralization with a basic or buffer solution to a pH between 5 and 7, so that the radio-pharmaceutical substance can be intravenously injected.

The main disadvantage of using stannous chloride is that it has a tendency to hydrolysis and oxidation. Hydrolysis is avoiding by using a strongly acid medium and oxidation is avoided by using deaerated solutions under nitrogen.

In practice, tagging is not often carried out by the medical team during clinical tests in the aforementioned extemporaneous manner. For convenience in clinical use, a number of international laboratories sell kits enabling the user to carry out his own tagging operations with a minimum of trouble. The preliminary operations of preparing and mixing the reagents are carried out by the laboratories, using large quantities of products at a time, which are then bottled with all necessary precautions, stored and supplied at request to medical teams. The user merely has to add the sterile TcO$_4$ solution at the time of the clinical examination.

Actually, this method of tagging by reduction by Sn$^{2+}$ is limited since the chosen excipient must of course always be an Sn$^{2+}$ chelating agent, so that tagging can be done at a pH between 5 and 7, the optimum region for injection. The reason is that hydrolysis of the stannous ion at the concentrations used occurs at a pH much lower than 5 and should be avoided. If the pH is higher, $^{99m}$Tc combines with the colloidal tin hydroxide formed and thus does not produce the required tagging.

It is an object of the invention to avoid the aforementioned disadvantages involved in using stannous chloride for reduction.

Accordingly, the present invention provides a method of using $^{99m}$Tc for tagging excipients in medical diagnosis by scintigraphy, which method comprises mixing, in an aqueous solution of alkali-metal pertechnetate, an excipient and a reducing agent present in a lower concentration and in the form of a complex, wherein the association constant of the anion with reduced technetium is less than the association constant of the excipient with reduced technetium, thus forming a radio-pharmaceutical substance which is a complex between the excipient and $^{99m}$ technetium.

In a preferred embodiment, the reducing complex is stannous pyrophosphate, and reduces the technetium in the Na $^{99m}$TcO$_4$ pertechnetate solution as follows:

The stannous ion of stannous pyrophosphate causes technetium to change from valency 7 to valency 4.

$$Tc_{VII} \rightarrow Tc_{IV}$$

$^{99m}$technetium IV combines with stannous pyrophosphate to form a chelate as follows:

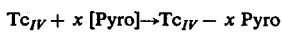

In accordance with the law of mass action, the association coefficient is:

$$K_1 = \frac{[T_{c_{IV}-x}\text{Pyro}]}{[T_{c_{IV}}][\text{Pyro}]^x}$$

A similar reaction occurs between $^{99m}$ Tc and the excipient (SV).

The association coefficient of the complex formed is:

$$K_2 = \frac{[Tc^{IV} - y\, SV]}{[Tc^{IV}][SV]^y}$$

Preferably K$_2$ is greater than K$_1$ and the SV pyro concentration ratio is also to the advantage of the excipient, so that the technetium separates from the pyrophosphate and combines with the excipient to give a high yield of the radio-pharmaceutical substance.

If $C_1$ denotes the concentration of $^{99m}$Tc combined with pyrophosphate and $C_2$ denotes the concentration of $^{99}$Tc combined with the SV, the ratio $K_2/K_1$ is:

$$\frac{K_2}{K_1} = \frac{C_2 \times [Pyro]^x}{C_1 \times [SV]^y}, \quad \frac{C_2}{C_1} = \frac{K_2}{K_1} \frac{[SV]_y}{[Pyro]^x}$$

The method according to the invention, therefore, is simpler than other methods known hitherto but its yield (as shown in the following examples) is equally high and applies even to excipients which do not chelate tin.

The following are examples of excipients which may be used: DTPA, bleomycin, albumin from human serum, erythrocytes, tetracycline, disodium citrate, polyphosphates, gluconate, dimercapto-succinate and, in general, all excipients used in nuclear medicine and satisfying the aforementioned conditions.

The method according to the invention is not only simpler in itself but also results in commercial products which are very easy to use.

Other features and advantages of the invention will be clear from the following description of some embodiments of the method applied to the tagging of a number of excipients, i.e. bleomycin, Ca-DTPA (calcium diethylene triamine pentaacetate), erythrocytes, and DMSA (dimercaptosuccinic acid).

In these examples, the reducing agent was stannous pyrophosphate, since it forms a relatively unstable complex with $^{99m}$ technetium. This instability can be measured by conveying a solution of tin pyrophosphate complex and $^{99m}$ technetium through a Sephadex column; it is found that 95% of the $^{99m}$ technetium remains fixed on the column.

The pyrophosphate solution used contained 1.66 mg $Na_4P_2O_7$, 10 $H_2O$ and 0.026 mg $SnCl_2$, 2 $H_2O$ per ml and its pH was approx. 6.

EXAMPLE 1

Bleomycin 1 ml saline solution of sodium pertechnetate containing 9 wt.% sodium was added to 15 mg lyophilised bleomycin. Next, 0.4 ml of stannous pyrophosphate solution was added, corresponding to 5 μg Sn II. The mixture was agitated in a centrifuge for about two minutes; the pH was equal to 5 without neutralizing being required.

The final product was analyzed by chromatography as follows:
1. On paper with a methanol/deaerated water (85/15) solvent to find the $NaTcO_4$ content, and
2. On a thin layer of alumina or silica gel with a 10% ammonium acetate and methanol (50/50) solvent for separating the different chemical species in solution.

The front ratios Rf, which can be defined as follows:

$$Rf = \frac{\text{distance travelled by the substance from the origin}}{\text{distance travelled by the solvent from the origin,}}$$

corresponding to 3 peaks for the following three categories of substances:
reduced $^{99m}$ Tc chelated with bleomycin,
reduced non-chelated $^{99m}$ Tc, and
non-reduced $^{99m}$Tc in the form of $^{99m}TcO_4$ — had the following values: (1) 0.0, 0.2/0.0/0.6; (2) 0.5, 0.7/0.0/0.8.

A study of the resulting three peaks showed that the content of reduced chelated $^{99m}$ Tc was 90%, a percentage which indicates the tagging yield, whereas the content of reduced non-chelated $^{99m}$ Tc was only 10% and there was no non-reduced technetium.

This example, incidentally, shows the superiority of the method according to the invention over the conventional method of reduction, using stannous chloride. The latter method gives a product having a pH of 2.5, which has to be neutralized before injecting a patient, and furthermore tests have shown that the yield of tagged bleomycin is only 44.4%, the content of reduced non-chelated $^{99m}$ Tc being 58.6%.

The method according to the invention, therefore can be used for tagging at a pH between 5 and 7, which is physiologically nearer to the optimum pH for intravenous injection, and also gives a better tagging yield. Clinical tests with the tagged product showed that the tagged compound behaves similar to $^{57}$ Co bleomycin conventionally used for detecting malign cerebral tumours. It was found that $^{99m}$ Tc does not show up the skeleton, thus providing that the $^{99m}$ Tc was in fact bonded to the bleomycin.

EXAMPLE 2

Calcium diethylene triamine pentaacetate (Ca DTPA)

The following solutions were added in succession:
1.8 ml calcium DTPA (containing 7.2 mg DTPA and 0.5 mg Ca), and 1 ml of a solution of $NaTcO_4$ obtained by extraction from a generator containing $^{99}$Mo. The mixture was agitated in a centrifuge for 1 to 2 minutes. Finally 0.5 ml of stannous pyrophosphate corresponding to 6 μg of $Sn^{II}$ was added.

The resulting mixture was analysed by conveying through a Sephadex column, which has the property of fixing and retaining the reduced $^{99m}$ Tc, whether chelated with pyrophosphate or not, whereas the DTPA-$^{99m}$ Tc complex is eluted. A determination by chromatography on paper was also made in a methanol-water (85/15) solvent medium. The results of these two operations showed the absence of pertechnetate and the presence of 5% reduced technetium not chelated with DTPA, i.e. the DTPA tagging yield was 95%.

EXAMPLE 3

Erythrocytes 1 ml stannous pyrophosphate solution (0.0665 mg Sn) was added to 1 ml of blood withdrawn on heparin, was left to incubate at room temperature for 10 minutes, centrifuged, and the erythrocytes were washed three times in 3 ml of 9 wt.% NaCl. 1 ml of $NaTcO_4$ solution was added, obtained by extraction from a generator containing $^{99}$Mo, and left to incubate at room temperature for 10 minutes.

Measurements were made of tagging after centrifuging and of the activity of the erythrocytes and of the supernatant liquid. The erythrocytes retained 97.2% of their activity and only approximately 0.3 - 1.2 was lost after they had been washed with 9 wt.% NaCl.

EXAMPLE 4

Dimercaptosuccinic acid (DMSA)

The contents of a bottle sold under the name TcK$_7$ by C I S for bone scintigraphy was dissolved in 3 ml of 0.9 wt.% NaCl. In addition, a solution of stannous pyrophosphate was obtained, corresponding to 84μg tin. A number of 0.3 ml samples were taken and introduced into a number of bottles before being lyophilised, so as to have tagging solutions ready at any instant.

The DMSA was tagged in the following two ways:

First Method:

0.3 ml stannous pyrophosphate solution was mixed with 3 ml of a solution of 0.9wt. % NaCl containing 1.6 mg DMSA.

Next, 3 ml of an NaTcO$_4$ solution obtained from a generator containing $^{99}$Mo was added, followed by strong agitation for 10 minutes.

Second Method:

3 ml of a 0.9 % NaCl solution containing 1.6 mg DMSA was poured into a bottle containing 0.3 ml lyophilised stannous pyrophosphate and stirred until it dissolved, after which 3 ml of a pertechnetate solution obtained from the generator containing $^{99}$Mo was added, followed by vigorous agitation for 10 minutes.

Tagging check

The final product was analyzed by chromatography on No. 1 Whatmann paper.

1. with methanol/deaerated water 85/15 (v/v) solvent
2. with 0.9% NaCl solvent, and
3. with 10% NH$_4$Cl solvent.

The Rf values for:

reduced $^{99m}$ Tc chelated with DMSA, reduced $^{99m}$ Tc, either not chelated or chelated with stannous pyrophosphate, and non-reduced $^{99m}$ Tc, i.e. in the state of TcO$_4$ $^-$, were the following, respectively:

0.0 – 0.0 – 0.5 for solvent 1
0.90 – 0.22 – 0.76 for solvent 2
0.90 – 0.1 – 0.79 for solvent 3.

Accordingly, the content of TcO$_4^-$ was less than 1.0, the content of reduced Tc not chelated with DMSA was less than 2% and the content of reduced Tc chelated with DMSA was above 97%.

Clinical tests:

The single drawing accompanying the present patent application shows, in the case of two patients, the variations in time in the elimination from the blood of pyrotechnetate injected alone (curve T$_1$ for the first patient and T$_2$ for the second patient) and of bleomycin complex tagged with $^{99m}$Tc by the method according to the invention (curve B$_1$ for the first patient and B$_2$ for the second patient). As can be seen, the bleomycin complex is eliminated on average twice as fast as pertechnetate.

Toxicity tests were made on mice. The LD 50, relative to the reducing reagent, was 100 mg/Kg.

What I claim is:

1. A method of using $^{99m}$Tc for tagging excipients in medical diagnosis by scintigraphy, which method comprises mixing, in an aqueous solution of alkalimetal pertechnetate, an excipient and a reducing agent complex present in a lower concentration, wherein the association constant of the anion of the reducing agent complex with reduced technetium is less than the association constant of the excipient with reduced technetium, thus forming a radio-pharmaceutical substance which is a complex between the excipient and $99^m$ technetium.

2. A method of tagging according to claim 1, wherein sodium pertechnetate in 9% NaCl saline solution is used.

3. A method of tagging according to claim 1, wherein the excipient is selected from among DTPA, bleomycin, albumin from human serum, erythrocytes, tetracycline, disodium citrate, polyphosphates, gluconate and dimercaptosuccinate.

4. A method of tagging according to claim 1, wherein stannous pyrophosphate is the reducing agent complex.

5. The method of claim 3, wherein said stannous pyrophosphate and said excipient are mixed together in a neutral aqueous solution prior to mixing with said solution of alkali-metal pertechnetate.

6. A method of tagging according to claim 4, wherein a solution of tin pyrophosphate is used at a pH between 5.5 and 6.5, corresponding to an Sn$^{II}$ content of approx. 5μg.

7. A method of tagging according to claim 4, wherein stannous pyrophosphate is used in solid form and in the form of a powder.

* * * * *